United States Patent
Tu et al.

(10) Patent No.: US 12,325,853 B1
(45) Date of Patent: Jun. 10, 2025

(54) PHYLLOBACTERIUM MYRSINACEARUM STRAIN N1N2-2 FOR EFFICIENT DEGRADATION OF DIPHENYLARSINIC ACID AND USE THEREOF

(71) Applicants: INSTITUTE OF SOIL SCIENCE, CAS, Nanjing (CN); CHINA CONSTRUCTION EIGHTH ENGRG DIVISION CORP. LTD, Shanghai (CN); China Construction Eighth Bureau Environmental Protection Technology Co., Ltd., Shanghai (CN)

(72) Inventors: Chen Tu, Nanjing (CN); Yongming Luo, Nanjing (CN); Ying Liu, Nanjing (CN); Runlai Luo, Nanjing (CN); Zhongyuan Li, Nanjing (CN)

(73) Assignees: Institute of Soil Science, CAS, Nanjing (CN); China Construction Eighth Engrg Division Corp. Ltd., Shanghai (CN); China Construction Eighth Bureau Environmental Protection Technology Co., Ltd., Shanghai (CN)

( * ) Notice: Subject to any disclaimer, the term of this patent is extended or adjusted under 35 U.S.C. 154(b) by 0 days.

(21) Appl. No.: 18/926,774

(22) Filed: Oct. 25, 2024

(30) Foreign Application Priority Data

Dec. 6, 2023 (CN) .......................... 202311665357.7

(51) Int. Cl.
*C12N 1/20* (2006.01)
*B09C 1/10* (2006.01)
*C02F 3/34* (2023.01)
*C02F 101/30* (2006.01)
*C12R 1/01* (2006.01)

(52) U.S. Cl.
CPC ................ *C12N 1/205* (2021.05); *B09C 1/10* (2013.01); *C02F 3/34* (2013.01); *C02F 2101/30* (2013.01); *C12R 2001/01* (2021.05)

(58) Field of Classification Search
None
See application file for complete search history.

(56) References Cited

PUBLICATIONS

Song et al., "Degradation characteristics of diphenylarsenic acid by Bacillus cerasus RC6B and its mutant strains," Microbiology China 44:2557-2566, 2017 (Year: 2017).*
Machine translation of Song et al., obtained from https://wswxtb.ijournals.cn/html/wswxtbcn/2017/11/tb17112557.htm on Jan. 15, 2025, 13 pages (Year: 2025).*
Chinese Patent Office Decision to Grant from application No. 202311665357 dated Jul. 8, 2024, 2 pgs.

* cited by examiner

*Primary Examiner* — David Steadman
(74) *Attorney, Agent, or Firm* — Tutunjian & Bitetto, P.C.

(57) ABSTRACT

A *Phyllobacterium myrsinacearum* strain N1N2-2 for efficient degradation of diphenylarsinic acid (DPAA) and use thereof are provided, relating to the technical field of microorganisms. The *Phyllobacterium myrsinacearum* strain N1N2-2 shows high tolerance and degradation efficiency to the DPAA, provides a microbial strain resource for the remediation and treatment of DPAA-contaminated soil and water environments, and has broad application prospects.

9 Claims, 3 Drawing Sheets

PHYLLOBACTERIUM MYRSINACEARUM STRAIN N1N2-2 FOR EFFICIENT DEGRADATION OF DIPHENYLARSINIC ACID AND USE THEREOF

CROSS-REFERENCE TO RELATED APPLICATION

This patent application claims the benefit and priority of Chinese Patent Application No. 202311665357.7 filed with the China National Intellectual Property Administration on Dec. 6, 2023, the disclosure of which is incorporated by reference herein in its entirety as part of the present application.

TECHNICAL FIELD

The present disclosure relates to the technical field of microorganisms, and in particular to a *Phyllobacterium myrsinacearum* strain N1N2-2 for efficient degradation of diphenylarsinic acid (DPAA) and use thereof.

BACKGROUND

Diphenylarsinic acid (DPAA) is one of the main organic arsenic pollutants in buried area soils and has high neurotoxicity and genotoxicity. DPAA shows strong stability and mobility in the environment and seriously endangers ecological environmental safety and human health. Therefore, there is an urgent need to conduct research on safe remediation technologies for soil contaminated by organic arsenic such as DPAA. Microbial remediation, due to its low cost, small environmental impact, and low risk of secondary pollution, has been widely used in soil and groundwater remediation. At present, research on the microbial degradation of DPAA is still relatively limited. There are technical problems such as a lack of effective microbial strain resources and low degradation efficiency. The low remediation efficiency has become one of the main bottlenecks restricting the application of microbial degradation.

SUMMARY

In order to solve the above problems, the present disclosure provides a *Phyllobacterium myrsinacearum* strain N1N2-2 for efficient degradation of DPAA and use thereof. The *Phyllobacterium myrsinacearum* strain N1N2-2 shows high tolerance and degradation efficiency to DPAA, provides a microbial strain resource for the restoration and treatment of DPAA-contaminated soil and water environments, and has broad application prospects.

To achieve the above objective, the present disclosure provides the following technical solutions The present disclosure provides a *Phyllobacterium myrsinacearum* strain N1N2-2 for efficient degradation of DPAA with a deposit number of CCTCC NO: M20232272.

The present disclosure further provides a microbial inoculant for degrading DPAA, including the *Phyllobacterium myrsinacearum* strain N1N2-2.

Preferably, the *Phyllobacterium myrsinacearum* strain N1N2-2 in the microbial inoculant has a viable count greater than or equal to $1 \times 10^6$ CFU/mL.

The present disclosure further provides a method for preparing the microbial inoculant, including the following steps:

inoculating the *Phyllobacterium myrsinacearum* strain N1N2-2 into a medium to allow scale-up culture to obtain the microbial inoculant.

Preferably, the medium includes an LB broth.

Preferably, the scale-up culture is conducted at 28° C. under 180 r/min to 250 r/min.

The present disclosure further provides the use of the *Phyllobacterium myrsinacearum* strain N1N2-2, the microbial inoculant, or a microbial inoculant prepared by the preparation method in degradation of DPAA.

The present disclosure further provides a method for degrading DPAA, including the following steps:

mixing the microbial inoculant with soil and/or water having DPAA.

Beneficial Effects

The present disclosure provides a *Phyllobacterium myrsinacearum* strain N1N2-2 for efficient degradation of DPAA with a deposit number of CCTCC NO: M20232272. The *Phyllobacterium myrsinacearum* strain N1N2-2 shows high tolerance and degradation efficiency to DPAA, can tolerate a high concentration (2 mg/L) of the DPAA, and can grow using the DPAA as a carbon source. The present disclosure provides a microbial strain resource for the restoration and treatment of DPAA-contaminated soil and water environments, and has broad application prospects.

DEPOSIT OF BIOLOGICAL MATERIAL

*Phyllobacterium myrsinacearum* strain N1N2-2 has been deposited at the China Center for Type Culture Collection (CCTCC), Wuhan University, No. 299, Bayi Road, Wuchang District, Wuhan, Hubei Province on Nov. 20, 2023, with a deposit number of CCTCC NO: M20232272.

BRIEF DESCRIPTION OF THE DRAWINGS

To describe the technical solutions in the examples of the present disclosure or in the prior art more clearly, the accompanying drawings required for the examples will be briefly described below.

DETAILED DESCRIPTION OF THE EMBODIMENTS

Figure 1:
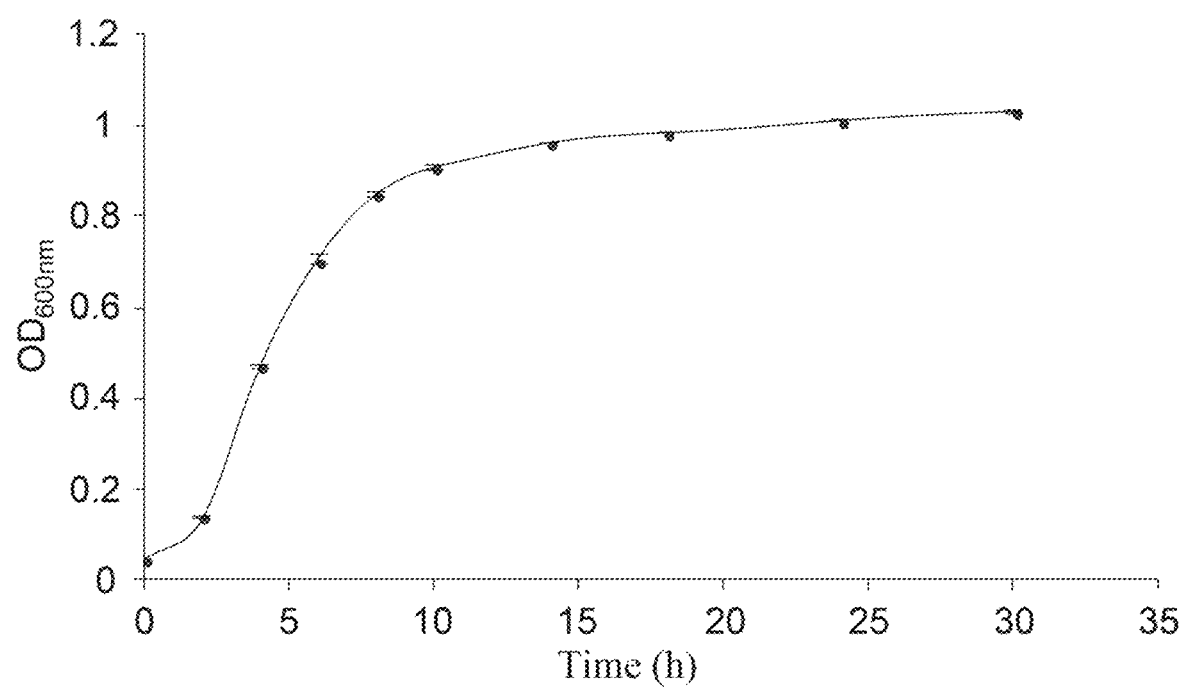
FIG. 1 shows the growth curve of an original strain RC6b.

The present disclosure provides a *Phyllobacterium myrsinacearum* strain N1N2-2 for efficient degradation of DPAA with a deposit number of CCTCC NO: M20232272.

In the present disclosure, the *Phyllobacterium myrsinacearum* strain N1N2-2 is a strain with high tolerance and degradation efficiency to DPAA and is constructed by genome shuffling with a *Phyllobacterium myrsinacearum* strain RC6b as an original strain, thereby providing microbial strain resources and ideas for the remediation and treatment of DPAA-contaminated soil and water environments. The *Phyllobacterium myrsinacearum* strain RC6b has a deposit number of CGMCC No. 6621 and is disclosed in Chinese patent CN201210412951.0.

The present disclosure further provides a microbial inoculant for degrading DPAA, including the *Phyllobacterium myrsinacearum* strain N1N2-2. In the present disclosure, the *Phyllobacterium myrsinacearum* strain N1N2-2 in the microbial inoculant has a viable count preferably greater than or equal to $1 \times 10^6$ CFU/mL.

The present disclosure further provides a method for preparing the microbial inoculant, including the following steps:

inoculating the *Phyllobacterium myrsinacearum* strain N1N2-2 into a medium to allow scale-up culture to obtain the microbial inoculant.

In the present disclosure, the medium preferably includes an LB broth; the scale-up culture is conducted at preferably 28° C. under preferably 180 r/min to 250 r/min, more preferably 180 r/min.

The present disclosure further provides the use of the *Phyllobacterium myrsinacearum* strain N1N2-2, the microbial inoculant, or a microbial inoculant prepared by the preparation method in degradation of DPAA.

The present disclosure further provides a method for degrading DPAA, including the following steps:

mixing the microbial inoculant with soil and/or water containing DPAA.

In the present disclosure, the *Phyllobacterium myrsinacearum* strain N1N2-2 shows high tolerance and degradation efficiency to DPAA, can tolerate a high concentration of DPAA, and can grow using DPAA as a carbon source. The strain can be used to remediate soil and water environments contaminated by DPAA and has broad application prospects.

In order to further illustrate the present disclosure, the *Phyllobacterium myrsinacearum* strain N1N2-2 for efficient degradation of DPAA and the use thereof provided by the present disclosure are described in detail below with reference to the accompanying drawings and examples, but the accompanying drawings and the examples should not be construed as limiting the protection scope of the present disclosure.

Example 1

1. Culture of Original Strain RC6b

A frozen glycerol stock of the original strain RC6b with a deposit number of CGMCC No. 6621 was taken out, a seed liquid thereof was dipped with an inoculation loop and inoculated on an LB plate for activation, and then cultured in an inverted manner in a constant-temperature incubator at 28° C. for 3 days. The activation medium was LB medium, including: NaCl 10.0 g/L, peptone 10.0 g/L, yeast extract 5.0 g/L, and agar powder 20 g/L, pH 6.8-7.0.

The physiological and biochemical characteristics of the strain RC6b were characterized, the morphological characteristics of the colonies on the plate were observed, and its growth curve was determined by turbidimetry.

Activation of the strain: fast-growing colonies were selected and inoculated into an LB broth, and cultured in a shaking incubator at 28° C. under 180 r/min until reaching a logarithmic growth phase.

The original strain RC6b on the LB plate was observed and found to have round, translucent, and milky white colonies with a plump and moist surface. The strain RC6b was stained red by Gram staining and was identified as a Gram-negative bacterium. FIG. 1 shows a growth curve of the original strain RC6b. The growth curve of the strain showed that the growth was relatively stable from 0 h to 2 h, which was a slow growth period; the growth showed an $OD_{600}$ value increased rapidly from 2 h to 10 h, which was a logarithmic growth period of the strain; after 10 h, the growth entered a stable period.

2. Chemical Mutagenesis of Original Strain RC6b

The strain was inoculated into an R2A broth and cultured in a shaking incubator at 28° C. under 180 r/min until reaching a logarithmic growth phase, a resulting bacterial solution was transferred into a centrifuge tube, centrifuged at 4,000 r/min for 10 min, and the bacterial cells were collected. The bacterial cells were washed 3 times with a 0.1 mol/L citrate buffer, resuspended with a citrate buffer containing 250 mg/L of a chemical mutagen, nitrosoguanidine, and incubated in a 37° C. constant-temperature water bath for 1 h. After incubation, the bacterial cells were collected by centrifugation, washed 2 times with 0.01 mol/L PBS buffer, resuspended in R2A medium, and cultured in a shaking incubator at 28° C. for 12 h. A cultured bacterial solution was spread on R2A solid medium by a dilution spread plate method and cultured in an inverted manner in a constant-temperature incubator at 28° C. The mutant strains were selected with rapid growth, neat edges, and large colony diameter to allow preservation.

Figure 2:
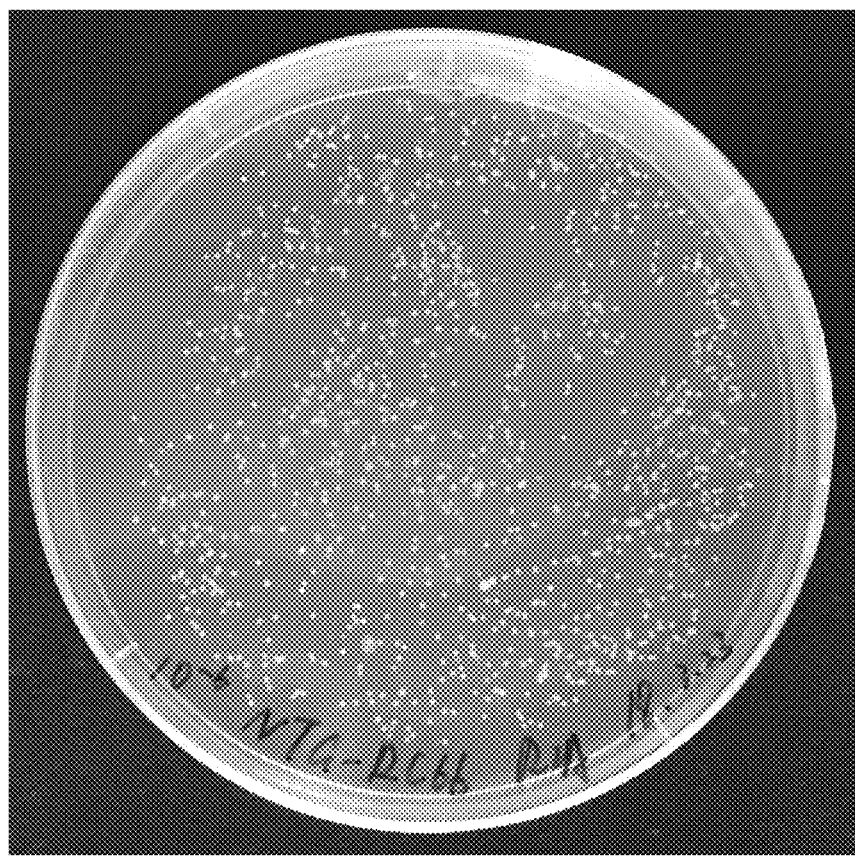
FIG. 2 shows a colony appearance of the original strain RC6b after chemical mutagenesis.

The colony appearance after nitrosoguanidine chemical mutagenesis is shown in FIG. 2. After mutagenesis, there was no change in the appearance of colonies, which were round, translucent, and milky white. Used reagents included the following components:

0.1 mol/L citrate buffer included: NaOH 8.8 g/L, citric acid 21.0 g/L, pH value adjusted to 5.5.

Nitrosoguanidine stock solution included: 0.01 g of nitrosoguanidine, 1.0 mL of acetone, and 9.0 mL of $H_2O$, filtered with a 0.22 μm sterile filter membrane after mixing.

Nitrosoguanidine mutagen included: the nitrosoguanidine stock solution was diluted with 0.1 mol/L citrate buffer to a concentration of 250 mg/L.

R2A medium included: $MgSO_4 \cdot 7H_2O$ 0.05 g/L, soluble starch 0.5 g/L, glucose 0.5 g/L, yeast extract 0.5 g/L, peptone 0.5 g/L, $K_2HPO_4$ 0.3 g/L, casamino acid 0.5 g/L, sodium pyruvate 0.3 g/L; 15-20 g/L agar powder was added into the solid medium.

3. Screening of Mutant Strain and Testing of Degradation Performance

Four mutant strains (NR-1, NR-2, NR-3, and NR-4) were selected with rapid growth and large colony diameter in step 2, cultured in LB medium until reaching a late logarithmic growth phase, and inoculated in mineral salt medium with DPAA as the sole carbon source at a 10% inoculation amount to allow shaking culture. At the same time, the original strain and inactivated strain treatments were also set up, and the inactivated strain treatment was used as a control. Samples were taken at the initial time, day 5, and day 10, and a DPAA content in the culture system and an OD value of the bacterial solution were determined. The $OD_{600}$ value of the bacterial solution was measured using a UV-visible spectrophotometer. The concentration of DPAA (purchased from WAKO®, Japan, purity 97%, CAS: 4656-80-8) in the solution was determined by high-performance liquid chromatography-tandem mass spectrometry (HPLC-MS/MS). Strains that could tolerate DPAA and had a higher degradation rate were selected as candidate strains for the next step.

$$\text{DPAA degradation rate (\%)} = \frac{\text{DPAA concentration in control group} - \text{DPAA concentration in experimental group}}{\text{DPAA concentration in control group}} \times 100\%$$

Used reagents included the following components:

Mineral salt medium included: $NH_4NO_3$ 0.5 g/L, $KH_2PO_4$ 1.0 g/L, $MgSO_4 \cdot 7H_2O$ 0.2 g/L, $FeSO_4 \cdot 7H_2O$ 0.005 g/L, vitamin solution 10.0 mL/L, trace element solution 10.0 mL/L, pH=7.0; where
- vitamin solution included: vitamin H 10.0 mg/L, calcium pantothenate 25.0 mg/L, niacin 100.0 mg/L, 4-aminobenzoic acid 500.0 mg/L, cyanocobalamin 20.0 mg/L, ammonium sulfate 50.0 mg/L, and pyridoxamine 250.0 mg/L; and
- trace element solution included: disodium EDTA 500.0 mg/L, $MnSO_4 \cdot H_2O$ 5.0 mg/L, $CoSO_4 \cdot 7H_2O$ 24.0 mg/L, $Na_2MoO_4 \cdot 2H_2O$ 5.0 mg/L, $ZnSO_4 \cdot 7H_2O$ 10.0 mg/L, $H_3BO_4$ 30.0 mg/L, $CuSO_4 \cdot 5H_2O$ 5.0 mg/L, and $Ca(OH)_2$ 50.0 mg/L.

Medium with DPAA as the sole carbon source: 2 mg/L DPAA was added into the mineral salt medium.

Figure 3:
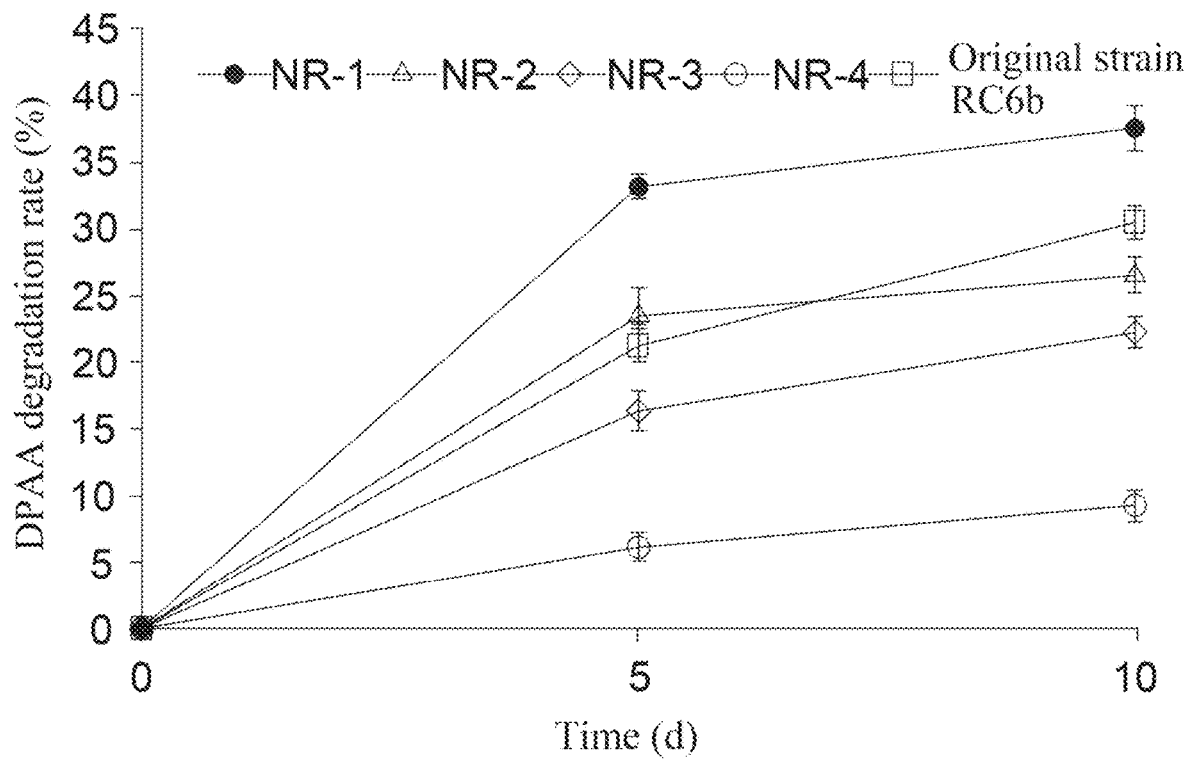
FIG. 3 shows a degradation rate of DPAA by a mutant strain.

NR-1, NR-2, and the original strain RC6b had high degradation rates for DPAA (FIG. 3). Among them, NR-1 always had a higher degradation rate for DPAA than the other four strains, with the DPAA degradation rate reaching 33.3% on the 5th day and 37.5% on the 10th day.

Table 1 Changes in $OD_{600}$ of strains in a culture system with DPAA alone as carbon source

| Strain | $OD_{600}$ | | |
|---|---|---|---|
|  | 0 d | 5 d | 10 d |
| RC6b | 0.240 ± 0.001 | 0.188 ± 0.001 | 0.179 ± 0.003 |
| NR-1 | 0.220 ± 0.018 | 0.112 ± 0.003 | 0.188 ± 0.005 |
| NR-2 | 0.235 ± 0.004 | 0.111 ± 0.003 | 0.204 ± 0.008 |
| NR-3 | 0.222 ± 0.007 | 0.096 ± 0.007 | 0.159 ± 0.014 |
| NR-4 | 0.239 ± 0.004 | 0.123 ± 0.004 | 0.193 ± 0.003 |

Figure 4:
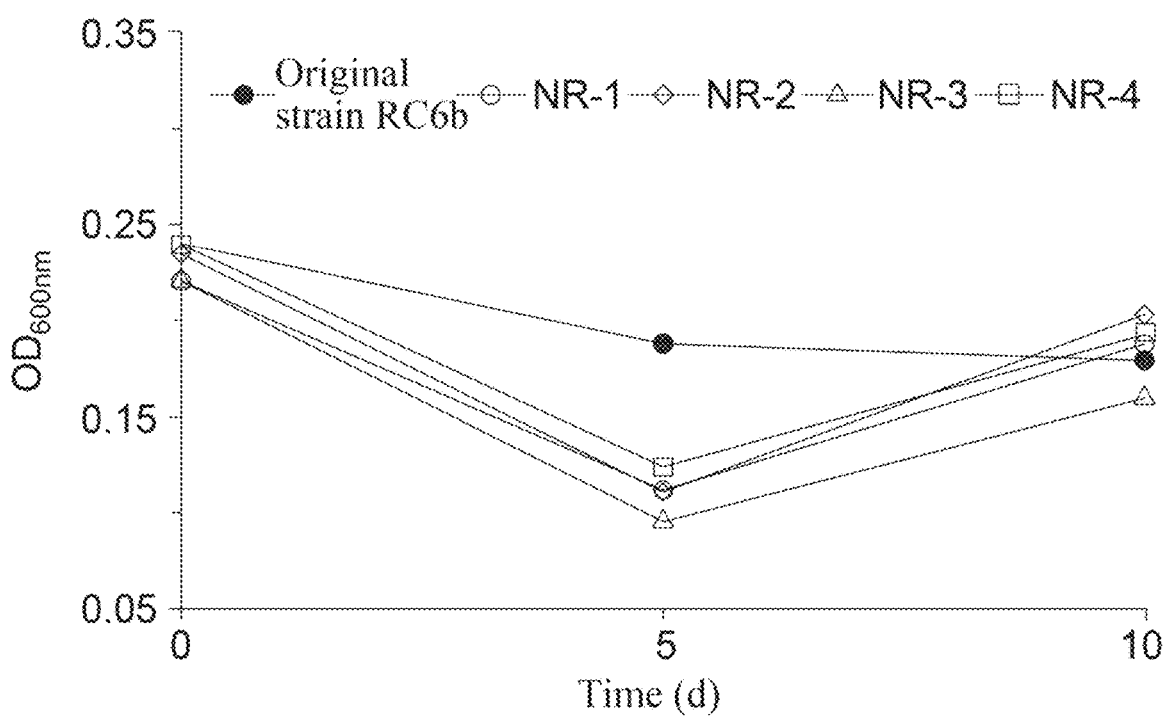
FIG. 4 shows $OD_{600}$ changes of the mutant strain in a DPAA-only carbon source system.

The growth conditions of the strain are shown in FIG. 4 and Table 1. When DPAA was the only carbon source, the $OD_{600}$ of the induced strain showed a trend of decreasing and then increasing. The $OD_{600}$ values of the 4 mutant strains dropped to the lowest point on the 5th day. On the 10th day, the $OD_{600}$ value of each of the mutant strains NR-1, NR-2, and NR-4 was higher than that of the original strain. It was the nitrosoguanidine mutagen that caused a favorable mutation in the strain RC6b, changed the metabolic mode of the strain RC6b to DPAA, and made the mutant strain begin to adopt DPAA for proliferation. Therefore, in the subsequent genome shuffling, NR-1 with the highest DPAA degradation rate was selected for protoplast fusion with the original strains RC6b and NR-2.

4. Genome Shuffling and Screening of Strain Genome (1) Preparation of Protoplasts The original strain and two mutant strains (NR-1 and NR-2) that grew rapidly and had high DPAA degradation rates in step 3 were selected for genome shuffling to prepare protoplasts of the parent strain.

10 mL of a bacterial solution cultured to the logarithmic growth phase was pipetted, centrifuged under 7,000 r/min at 4° C. for 5 min, the supernatant was discarded, the bacterial cells were washed 2 times with 0.01 mol/L PBS buffer, and resuspended with 10 ml of protoplast stabilization solution. 5 mL of bacterial suspensions of the parent strain RC6b, NR-1, and NR-2 were taken separately, mixed evenly with 5 mL of lysozyme solution, heated in a constant-temperature water bath at 37° C. for 40 min, and samples were taken to allow microscopic examination every 10 min. When more than 90% of the bacterial cells became spherical protoplasts, the centrifuge tube was centrifuged at 5,000 r/min for 10 min and the supernatant was discarded. The lysozyme was removed by washing with a hypertonic buffer, and the protoplasts were resuspended. The bacterial cells were collected by centrifugation at 2,500 r/min for 5 min and then suspended in protoplast stabilization solution.

Protoplast stabilization solution (mol/L) included: $MgCl_2$ 0.02, maleic acid 0.02, and sucrose 0.5, pH value adjusted to 6.5.

Lysozyme solution (g/L) included: lysozyme 10.0, maleic acid 2.32, sucrose 171.15, and $MgCl_2$ 1.90, sterilized by filtration.

Hypertonic buffer (g/L) included: $NaH_2PO_4$ 8.3, $Na_2HPO_4$ 4.8, and mannitol 145.7.

(2) Fusion of Protoplasts 2 mL protoplast suspension of the mutant strain NR-1 was mixed with the protoplast suspension of NR-2 and the protoplast suspension of the original RC6b, then allowed to stand for 5 min, centrifuged at 3,000 r/min for 10 min, and the supernatant was discarded. 200 μL of the protoplast stabilization solution was added to the centrifuge tube and mixed, and then 1,800 μL of the PEG solution was added, and the resulting mixture was gently shaken, heated in a 37° C. constant-temperature water bath for 2 min, and centrifuged at 3,000 r/min for 10 min to collect the bacterial cells, and the fused recombinant bacterial cells were resuspended in 2 mL of the protoplast stabilization solution. The fused bacterial solution was diluted with protoplast stabilization solution to a dilution of $10^{-4}$, $10^{-5}$, and $10^{-6}$, and 100 μL of the diluted fused bacterial solution was applied to the hypertonic regeneration solid medium and then cultured in a 28° C. constant-temperature incubator for 48 h. The colony appearance and size of the recombinant strain were observed, and a genome-shuffling strain with rapid growth was selected to allow preservation.

Fusion promoting agent, PEG solution included: PEG-4000 with a final volume concentration of 40% was added to the protoplast stabilization solution, and sterilized at 115° C. for 20 min.

Hypertonic regeneration solid medium included: NaCl 35.0 g/L, peptone 10.0 g/L, beef extract 5.0 g/L, yeast powder 5.0 g/L, glucose 5.0 g/L, mannitol 45.5 g/L, $MgCl_2 \cdot 6H_2O$ 4.1 g/L, and gelatin 20.0 g/L, pH=7.0-7.2, sterilized at 115° C. for 20 min.

(3) Screening of Genome Shuffling Strain

Figure 5:
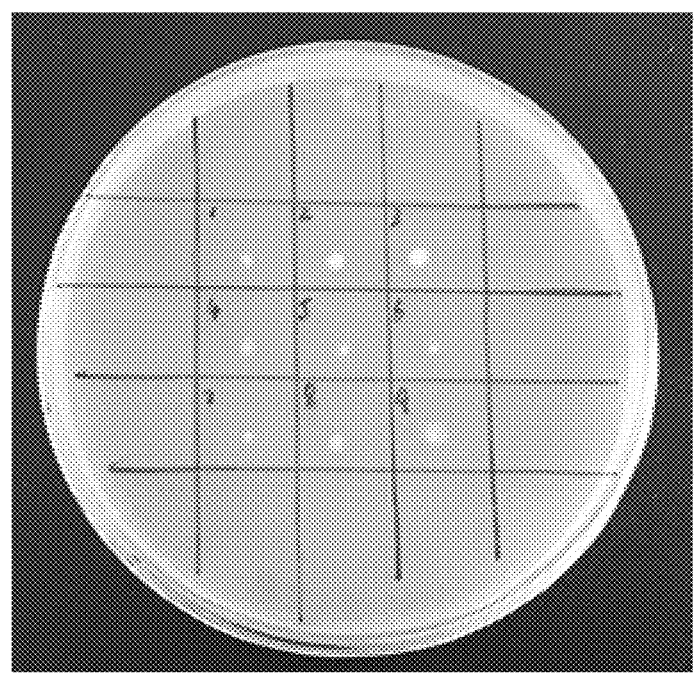
FIG. 5 shows the growth results of a parent strain and a recombinant strain on a plate with DPAA as the sole carbon source.

Preliminary screening by spotting method: the fused recombinant strain was grown on the plate with a 100 μL pipette tip and lightly dipped on the mineral salt medium with DPAA-only carbon source, while the parent strain (original strain RC6b) was set up as a control group, the plate was subjected to inverted culture in a constant-temperature incubator at 28° C., and the growth of each colony was observed. The initial screening was completed by selecting colonies that could grow faster on the plates containing DPAA as the sole carbon source (FIG. 5).

Figure 6:
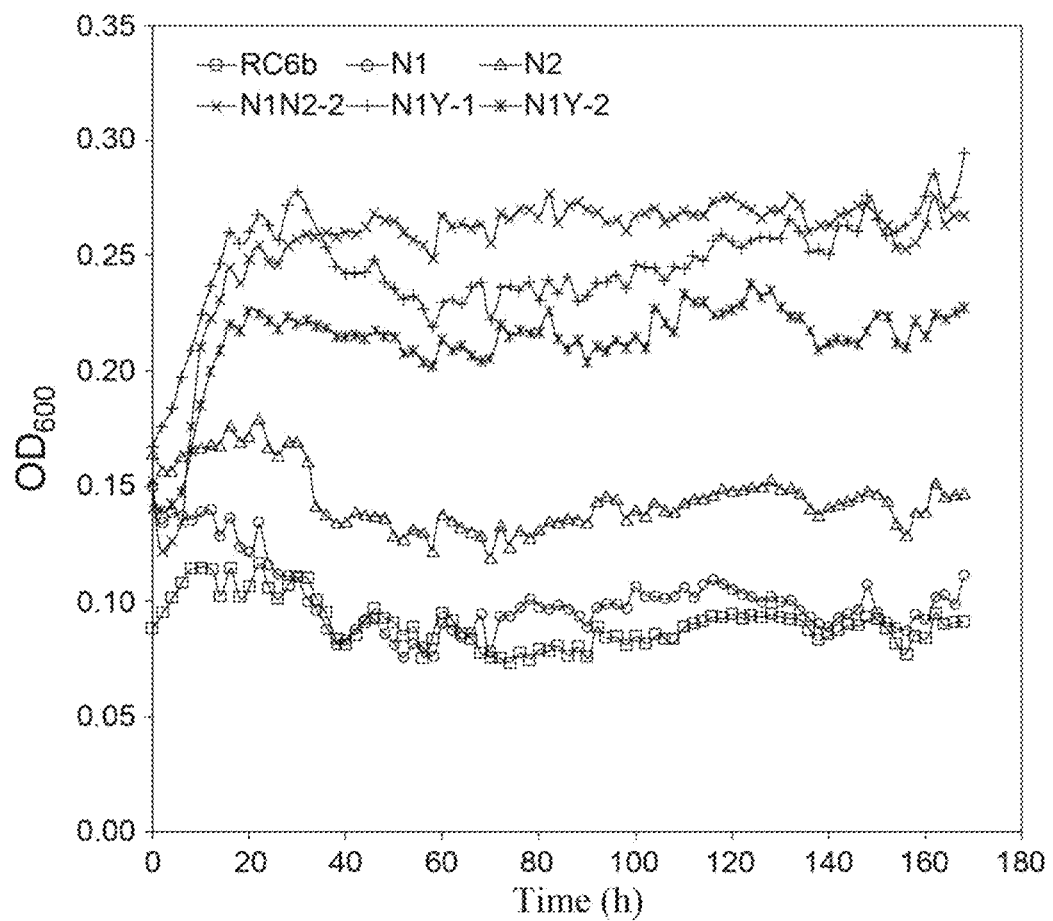
FIG. 6 shows a growth curve of the recombinant strain obtained through secondary screening.

Secondary screening: strains with faster growth were selected in the preliminary screening, and the secondary screening was conducted on the obtained recombinant strain by measuring the growth curve of the strains in mineral salt medium with DPAA as the sole carbon source, so as to verify the tolerance and degradation ability of the efficient degrading strains to DPAA. A specific process was as follows:

The initially screened colonies that could grow rapidly were used as a target strain transferred to 20 mL of LB medium and cultured to the logarithmic growth phase, centrifuged at 4,000 r min$^{-1}$ for 10 min, the bacterial cells were collected and washed 2 times with mineral salt medium, and the initial OD$_{600}$ value was adjusted to 1.0. 40 µL of bacterial solution was transferred to a supporting well plate of the Bioscreen C (FP-1100-C) growth curve measuring instrument, and 360 µL of the DPAA-sole carbon source medium was added to measure the growth curve of the strain (FIG. 6). The strain (N1N2-2) that could grow rapidly was a target strain constructed for DPAA efficient degradation, and the N1N2-2 was deposited in the China Center for Type Culture Collection (CCTCC), with a deposit number of CCTCC NO: M20232272.

Although the above example has described the present disclosure in detail, they are only a part of, not all of, the examples of the present disclosure. Other examples may also be obtained by a person skilled in the art based on the examples without creative efforts, and all of these examples shall fall within the protection scope of the present disclosure.

What is claimed is:

1. A microbial inoculant for degrading diphenylarsenic acid (DPAA), comprising a *Phyllobacterium myrsinacearum* strain N1N2-2 wherein the *Phyllobacterium myrsinacearum* strain N1N2-2 has been deposited at the China Center for Type Culture Collection with the deposit number of CCTCC M20232272.

2. The microbial inoculant according to claim 1, wherein the *Phyllobacterium myrsinacearum* strain N1N2-2 in the microbial inoculant has a viable count greater than or equal to 1×10$^6$ CFU/mL.

3. A method for preparing the microbial inoculant according to claim 1, comprising:
   inoculating the *Phyllobacterium myrsinacearum* strain N1N2-2 into a medium to allow scale-up culture to obtain the microbial inoculant.

4. The method according to claim 3, wherein the medium comprises an LB broth.

5. The method according to claim 3, wherein the scale-up culture is conducted at 28° C. under 180 r/min to 250 r/min.

6. A method for degrading DPAA, comprising:
   mixing the microbial inoculant according to claim 1 with soil and/or water having the DPAA.

7. A method for preparing the microbial inoculant according to claim 2, comprising:
   inoculating the *Phyllobacterium myrsinacearum* strain N1N2-2 into a medium to allow scale-up culture to obtain the microbial inoculant.

8. The method according to claim 4, wherein the scale-up culture is conducted at 28° C. under 180 r/min to 250 r/min.

9. A method for degrading DPAA, comprising:
   mixing the microbial inoculant according to claim 2 with soil and/or water having the DPAA.

* * * * *